(12) United States Patent
O'Connor

(10) Patent No.: US 8,712,012 B2
(45) Date of Patent: Apr. 29, 2014

(54) COMBINED IMAGING AND RADIATION THERAPY

(75) Inventor: John P. O'Connor, Andover, MA (US)

(73) Assignee: Analogic Corporation, Peabody, MA (US)

( * ) Notice: Subject to any disclaimer, the term of this patent is extended or adjusted under 35 U.S.C. 154(b) by 352 days.

(21) Appl. No.: 13/171,055

(22) Filed: Jun. 28, 2011

(65) Prior Publication Data

US 2013/0003930 A1 Jan. 3, 2013

(51) Int. Cl.
*G21K 5/08* (2006.01)
(52) U.S. Cl.
USPC ............. 378/68; 378/65; 378/208; 378/209
(58) Field of Classification Search
USPC ............ 378/65, 68, 208, 209; 600/425, 427
See application file for complete search history.

(56) References Cited

U.S. PATENT DOCUMENTS

| | | | |
|---|---|---|---|
| 2,781,454 A | 2/1957 | Green et al. | |
| 5,574,763 A | 11/1996 | Dehner | |
| 5,668,371 A | 9/1997 | Deasy et al. | |
| 6,307,914 B1 | 10/2001 | Kunieda et al. | |
| 6,385,288 B1 | 5/2002 | Kanematsu | |
| 6,560,310 B2 | 5/2003 | Stark | |
| 6,842,502 B2 | 1/2005 | Jaffray et al. | |
| 7,221,733 B1 | 5/2007 | Takai et al. | |
| 7,310,404 B2 | 12/2007 | Tashiro et al. | |
| 7,526,066 B2 | 4/2009 | Koshnitsky et al. | |
| 7,634,057 B2 | 12/2009 | Ein-Gal | |
| 7,640,607 B2 | 1/2010 | Guertin et al. | |
| 7,796,730 B2 | 9/2010 | Marash et al. | |
| 7,847,275 B2 | 12/2010 | Lifshitz et al. | |
| 7,953,205 B2 | 5/2011 | Balakin | |
| 2006/0285639 A1 | 12/2006 | Olivera et al. | |
| 2008/0317203 A1 | 12/2008 | Ferrand et al. | |
| 2010/0074400 A1* | 3/2010 | Sendai | 378/37 |

OTHER PUBLICATIONS

Amendment after Final cited in U.S. Appl. No. 12/551,024 dated Jan. 25, 2013, 9 pgs.
Final Office Action cited in U.S. Appl. No. 12/551,024 dated Oct. 25, 2012, 13 pgs.
Non-Final Office Action in Related U.S. Appl. No. 12/551,024 Dated—Feb. 4, 2011.
Response to Non-Final Office Action cited in related U.S. Appl. No. 12/551,024, filed Jul. 24, 2012, pp. 1-12.
Response to Non-Final Office Action cited in related U.S. Appl. No. 12/551,024 dated May 5, 2011.
Non-Final Office Action cited in related U.S. Appl. No. 12/551,024 dated Jul. 15, 2011.

(Continued)

*Primary Examiner* — Courtney Thomas
(74) *Attorney, Agent, or Firm* — Cooper Legal Group LLC

(57) ABSTRACT

One or more techniques and/or systems described herein provide for examining an object (e.g., a tumor in a patient) and subsequently treating the object. The examination and treatment generally occur very close to one another in time, with the patient remaining on a support article (e.g., on a bed or in a chair) during both the examination and the treatment. In this way, a position of the tumor and/or orientation of the tumor relative to the patient is substantially fixed during both the examination and the treatment. In one embodiment, a support article is configured to rotate during the examination and/or treatment. In this way, the object can be examined (e.g., and volumetric data related to the object can be acquired) and/or treated without moving portions of the imaging and/or treatment apparatus, for example.

20 Claims, 4 Drawing Sheets

(56) References Cited

OTHER PUBLICATIONS

Response to Non-Final Office Action cited in related U.S. Appl. No. 12/551,024 dated Oct. 17, 2011.
Final Office Action cited in related U.S. Appl. No. 12/551,024 dated Oct. 27, 2011.
Response to Final Office Action cited in related U.S. Appl. No. 12/551,024 dated Jan. 27, 2012.
Non-Final Office Action cited in related U.S. Appl. No. 12/551,024 dated Apr. 24, 2012.
Notice of Allowance cited in U.S. Appl. No. 12/551,024 dated Feb. 5, 2013, 13 pgs.

* cited by examiner

COMBINED IMAGING AND RADIATION THERAPY

BACKGROUND

The present application relates to the examination and treatment of objects. It finds particular application in breast cancer, testicular cancer and/or prostate cancer detection and treatment. It also relates to other medical applications where imaging systems are used to identify tumors and/or other treatment regions of an object that are subsequently treated using radiation therapy systems.

Cancer is one of the leading causes of death in humans. Advancements in medical technologies have played an intricate role in both identifying tumors in the early stages and treating the tumors by either slowing their growth or shrinking tumors to a size that can safely be removed or possibly extinguished. These advancements have also identified techniques and/or systems that are less invasive and less uncomfortable to a patient undergoing treatment than techniques and/or systems used in years past.

Numerous techniques such as chemotherapy and radiation therapy have been developed to shrink and/or eradicate cancerous cells once they are detected. In radiation therapy, photons and/or particles are used to penetrate the patient's tissue and treat cancerous cells. Beams of photons and/or particles are targeted at the cancerous tumor and are configured to damage the DNA of tissue cells. Because tumors are generally not able to repair damaged DNA and/or repair damaged DNA more slowly than non-tumor cells, the beams may ultimately cause the cells to die (e.g., causing the tumor to shrink, possibly to the point of extinction).

The type of radiation therapy that is used to treat tumors generally depends upon the location of the tumor because particle treatment systems, while more controllable, are generally more costly to manufacture and operate. For example, tumors that are near and/or comprised within vital organs (e.g., such as the brain, spine, etc.) are generally treated with particle treatment systems because the energy of the radiation dose can be controlled (e.g., such that the energy peaks as the particle is passing through the cancerous cells while remaining relatively low before and/or after it impacts the cancerous cells). Tumors that are not as proximate to vital organs (e.g., such as breast cancer, prostate cancer, and/or other cancers that develop in a patient's extremities) are generally treated using photon therapy systems because less precision is required and because such treatments are relatively inexpensive.

It can be appreciated that before treating a patient with radiation therapy a treatment plan is generally developed to identify a specific target region. To generate a treatment plan, a patient is examined using an imaging apparatus (e.g., such as a computed tomography (CT) scanner, an MRI scanner, an ultrasound device, etc.). Such a treatment plan may specify the orientation of the tumor in the patient, the desired trajectory of the treatment beams relative to the patient, the dose of the radiation, etc., for example.

Typically, days, if not weeks, after the imaging is performed and the treatment plan is developed, the patient begins treatment. Radiographic treatments generally involve exposing the tumor, or a treatment region (e.g. which may be larger than the tumor) to radiographic photons (e.g., of a higher dose than the exposure during imaging) and/or radiographic particles.

While the existing techniques have proven effective for treating numerous types of tumors, there are some disadvantages. For example, the imaging and treatment do not generally occur concurrently, and thus the orientation of the tumor may vary slightly between the imaging and the treatment (e.g., the patient may be in a slightly different position during the treatment). Moreover, in some applications, the orientation of the patient differs because the imaging and the treatment are done with the patient at different positions. For example, with respect to breast cancer treatment applications, the imaging is generally performed with the patient in an upright position and the treatment is generally performed with the patient in a horizontal position (e.g., laying on her/his back). It will be appreciated to those skilled in the art that to compensate for such orientation changes in the tumor between the imaging and the treatment, the target or treatment area is generally larger than the actual tumor. Therefore, the patient is exposed to radiation that would be unnecessary if the orientation of the tumor could be more precisely known during the treatment.

SUMMARY

Aspects of the present application address the above matters, and others. According to one aspect, an apparatus is provided. The apparatus comprises an imaging apparatus configured to examine an object. The apparatus also comprises a treatment apparatus configured to develop a treatment plan based at least in part upon the examination of the object and to treat the object according to the treatment plan. The apparatus also comprises a support article configured to support the object in a substantially same orientation relative to the support article during both the examination and the treatment, the support article comprising one or more receptors for receiving at least a portion of the object that is under the examination and the treatment.

According to another aspect, a method is provided. The method comprises examining an object situated on a support article to develop a treatment plan. The method also comprises treating the object based upon the treatment plan while the object remains situated on the support article, the treatment based at least in part upon the examination, the support article substantially affixed to a floor of an operation room during both the examination and treatment.

According to yet another aspect, an apparatus for treating at least one of breast cancer, prostate cancer and testicular cancer is provided. The apparatus comprises a support article comprising a receptor for receiving at least one of breast tissue, prostate tissue and testicular tissue. The apparatus also comprises an imaging apparatus configured to examine at least one of the breast tissue, the prostate tissue and the testicular tissue while the patient is supported by the support article. The apparatus further comprises a treatment apparatus configured to treat at least one of the breast tissue, the prostate tissue and the testicular tissue while the patient is supported by the support article. The support article is configured to pivot about an axis during at least one of the examination and the treatment, causing a position of at least one of the breast tissue, the prostate tissue and the testicular tissue to change relative to at least one of the imaging apparatus and the treatment apparatus. The examination and the treatment are performed while the patient remains in substantially fixed orientation relative to the support article.

Those of ordinary skill in the art will appreciate still other aspects of the present application upon reading and understanding the appended description.

FIGURES

The application is illustrated by way of example and not limitation in the figures of the accompanying drawings, in which like references indicate similar elements and in which.

DESCRIPTION

Figure 1:
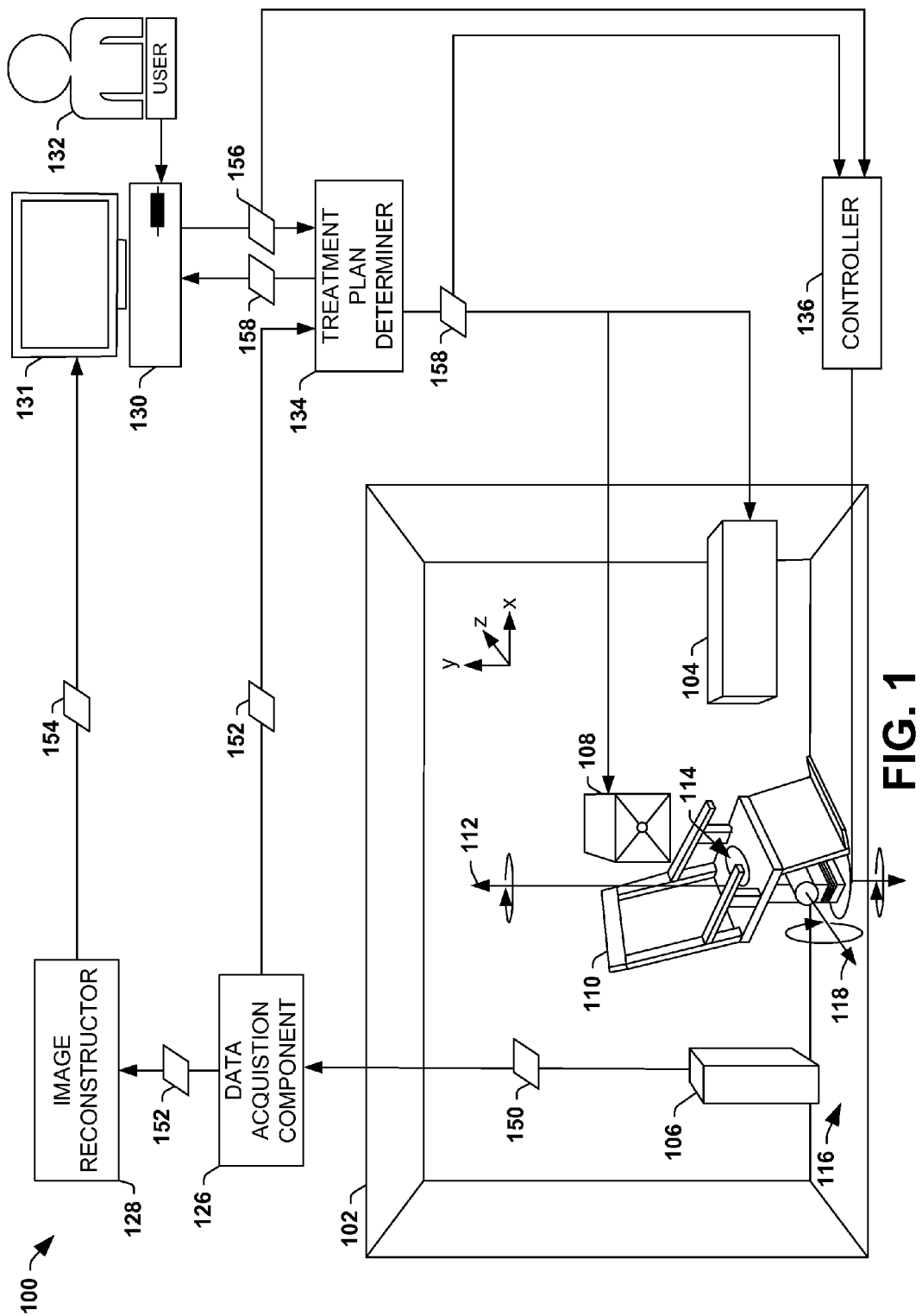
FIG. 1 is a schematic block diagram illustrating an example environment for examining an object and treating the object using radiation.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

One or more systems and/or techniques for imaging a patient using an imaging system, such as a radiographic imaging system (e.g., a flat panel detector array system, a computed tomography (CT) system, etc.), MRI system, and/or ultrasound system, for example, and treating a patient using a radiation treatment system (e.g., a particle therapy system or a photon therapy system) are provided herein. Generally, the imaging and the treatment are performed substantially concurrently and/or close in time (e.g., with the treatment beginning within a few minutes or less after examining the object/patient via imaging), with the patient remaining in a substantially same orientation and/or position during both the imaging and the treatment. That is, the patient is generally substantially immobilized during the imaging and the subsequent treatment, so that the orientation/position of the tumor relative to the patient does not change between the imaging and the treatment. In this way, the patient, or rather merely portions of the patient proximate the tumor, can be imaged, a treatment plan can be developed, and the patient can be treated during a single sitting. It will be appreciated that such techniques and/or systems provide numerous benefits over the conventional imaging and treatment techniques. For example, because the imaging and treatment are performed substantially concurrently (e.g., within a matter of seconds or minutes of each other) the position of the tumor remains substantially fixed, and thus, the size of the treatment zone or target region relative to the size of the tumor can be reduced (e.g., to exclude more healthy tissue). Moreover, if the imaging is performed before respective treatments (e.g., which has conventionally not been done), the treatment region can be altered based upon alterations in the tumor (e.g., as the size of the tumor shrinks or expands, the treatment region can be reduced, enlarged or otherwise varied).

FIG. 1 is an illustration of an example environment 100 of an apparatus which may be employed for imaging an object to create a treatment plan and/or for treating an object (e.g., a human patient or animal) (not illustrated). For example, in one embodiment, such an environment 100 may be used to image and/or treat breast cancer, testicular cancer, prostate cancer, etc. using various forms of radiation. Generally, one or more two- and/or three-dimensional images of an object are generated using an imaging apparatus, a treatment plan is developed for treating a tumor identified in the images, and a treatment is performed according to the treatment plan using a radiation therapy system.

It will be appreciated that while reference is routinely made to computed tomography (CT) imaging apparatus herein, other imaging apparatuses known to those skilled the art (e.g., for imaging tumors) are also contemplated herein. For example, an imaging apparatus may comprise but is not limited to flat panel detector systems, ultrasound systems and/or magnetic resonance imaging (MRI) systems, for example. Thus, numerous imaging systems for imaging tumors (e.g., or other objects) are known to those skilled in the art, and the type of imaging apparatus that is used may depend upon the type of tumor, the location of the tumor, and/or other variables known to those of skill in the art.

It will also be appreciated that the type of radiation therapy system may vary according to the application, the location of the tumor, etc. For example, tumors that are proximate the brain, spine, and/or other vital organs may be treated with a particle (e.g., proton) therapy system whereas tumors that are less proximate to vital organs, such as breast and prostate cancer, for example, may be treated with photon therapy systems. Thus, to the extent practical, the scope of the disclosure, including the scope of the claims, is not intended to be limited to a particular type or form of imaging system and/or to a particular type or form of radiation therapy system.

The example environment 100 comprises an operation room 102 within which a patient may be examined (e.g., to develop a treatment plan) and treated. The operation room 102 comprises an imaging apparatus (e.g. comprised of a radiation source 104 and a detector array 106), a treatment apparatus 108, and a support article 110 (e.g. a chair, bed, etc.) configured to support the object during both the examination and subsequent treatment. By way of example, the patient sits in the support article 110, which may be configured to rotate about an axis 112 in the y-dimension, for example, while the patient, or more particularly the tumor, is examined or imaged by the imaging apparatus and treated by the treatment apparatus. Thus, the patient remains at a substantially fixed orientation relative to the support article (e.g., the relative orientation of the support article and the object remain substantially constant) during both the examination and the treatment.

The support article 110 may be configured based upon the type of cancer treatment the operation room 102 is intended to treat. For example, the support article 110 may be comprised one or more receptors 114 (e.g., a hole, cavity, or other opening) through which an extremity comprising a tumor (e.g., testicular tissue, prostate tissue, breast tissue, etc.) may reside while undergoing treatment in the operation room 102. That is, in one embodiment, the support article 110 may comprise a receptor 114 for receiving a portion of the object (e.g., the tumor) under examination. By way of example, in the illustrated embodiment, the operation room 102 may be configured to treat prostate cancer and/or testicular cancer and the support article 110 may comprise a receptor for receiving prostate tissue and/or testicular tissue (e.g., such that the tissue is positioned away from the patient's other tissues). It will be appreciated that other configurations for the support article (e.g., such as, but not limited to, those illustrated in FIGS. 2-3) are also contemplated herein.

Moreover, in one embodiment, the support article 110 may be affixed to (e.g., fastened to, coupled to, etc.) a floor 116 of the operation room 102. That is, in one embodiment, while the support article 110 may rotate about a y-axis 112, the support article 110 may remain in a substantially stationary position during the examination and subsequent treatment of the object. It will be appreciated that while reference is made to the support article 110 being affixed to the floor 116, the support article 110 may still have limited movement relative to the floor 116. For example, the support article 110 may be affixed to tracks, and the tracks may be affixed to the floor 116 of the operation room 102. Thus, the support article 110 may be able to glide along the tracks while still being affixed to the floor 116 (e.g., such that the support article 110 cannot move freely about the operation room 102 (e.g., in a direction that tracks do not go) and/or be moved into other operation rooms (e.g., not connected by tracks), for example.

The illustrated imaging apparatus comprises a radiation source 104 configured to emit x-ray radiation in the form of a fan, cone, or other shaped radiation beam(s) towards the object upon which the operation is performed (e.g., the object under examination). As illustrated, the x-ray radiation generally travels through one or more planes substantially parallel to a plane of the floor 116 of the operation room 102. That is, in the illustrated example, x-ray radiation may be configured to be emitted along a substantially horizontal trajectory such that, upon its exit from the radiation source 104, the x-ray radiation traverses a patient situated on the support article 110 and impinges the detector array 106 situated on a substantially opposite side of the patient relative to the radiation source 104. It will be appreciated that, as described below, in another embodiment, the x-ray radiation may follow a different trajectory, such as a substantially vertical trajectory, for example.

The illustrated imaging apparatus also comprises a detector array 106 configured to detect x-ray radiation that was emitted from the radiation source 104 and that has traversed the patient under examination. The detector array 106 is generally comprised of a plurality of pixels or channels that detect x-ray radiation 116 and output signals 150 indicative of the detected radiation, or indicative of the attenuation of the radiation as it traversed the patient.

It will be appreciated that where the imaging apparatus comprises a detector array 106, the size and/or the shape of the detector array 106 may depend upon the type of imaging apparatus being used to examine the patient and/or the type(s) of images that are to be formed from the examination, for example. In one embodiment, where two-dimensional images are to be generated, a flat-panel detector array (e.g., similar to that illustrated in FIG. 1) comprising a flat detection surface (e.g., which faces the radiation source 104) may be employed. In other embodiments, such as where volumetric information related to the object under examination (e.g., the tumor) is to be acquired, the detector array 106 may have a curved detector surface, for example. Thus, the instant disclosure, including the scope of the claims, is not intended to be limited to a particular type of detector array. Rather, the type of detector array 106 that an imaging apparatus comprises (e.g., if it comprises one at all) may depend upon numerous implementation details such as the type/location of the tumor being examined/treated, whether two-dimensional or three-dimensional information about the object will be sufficient to generate an adequate treatment plan, etc.

It will be appreciated to those skilled in the art that in order to generate volumetric data, the object generally is viewed from a plurality of angles or perspectives. Thus, in at least some embodiments, at least one of the imaging apparatus (e.g., the radiation source 104 and/or the detector array 106) and the patient are generally rotated if volumetric information about the object under examination is desired. In the illustrated embodiment, the support article 110 is configured to rotate, or pivot, about an axis of rotation 112 (e.g., the y-axis), also referred to herein as a center point of rotation, while the radiation source 104 and the detector array 106 remain substantially stationary. That is, in one embodiment, the respective orientation of the object under examination and the imaging apparatus changes by rotating the support article 110 (e.g., and thus the object/patient) while holding fixed the position of the imaging apparatus (e.g., the radiation source 104 and the detector array 106). In another embodiment, the imaging apparatus may be attached to a rotating gantry (not shown) and may be configured to rotate about the object while the support article 110 (e.g., and thus the patient) remain substantially stationary. And, in yet another embodiment, the imaging apparatus and the support article 110 may be configured to rotate (e.g., at least intermittently) during the examination.

Moreover, as described in the particular embodiment above, the beams of x-rays may follow different trajectories according to the application (e.g., the cancer being treated) and/or based upon details of the implementation. Thus, the position of the radiation source 104 and/or the detector array 106 may vary from that illustrated herein. For example, in some embodiments, such as in the treatment of prostate cancer and/or testicular cancer, a horizontal configuration of the radiation source 104 and the detector array 106 may be preferred (e.g., where the x-ray radiation travels substantially horizontally). In other embodiments, a vertical configuration of the radiation source 104 and the detector array 106 may be preferred (e.g., where the radiation source 104 is above the patient, the detector array 106 is below the patient, and the x-ray radiation travels substantially vertically (in the y-direction)). Further, if the imaging apparatus comprises a rotating gantry (not shown), the rotating gantry may rotate (in an x-z plane) about an axis substantially extending in the y-direction (e.g., and referred to as a horizontal scanner) if the radiation source 104 and the detector array 106 are in a horizontal configuration. Alternatively, the rotating gantry may rotate (in a y-z plane) about an axis substantially extending in the x-direction (e.g., and referred to as a vertical scanner) if the radiation source 104 and the detector array 106 are in a vertical configuration.

By way of example, in one embodiment (e.g., where prostate cancer and/or testicular cancer is being examined), the imaging apparatus (e.g., which may include the radiation source 104 and the detector array 106) is fixed (e.g., to walls or a floor 116 of the operation room 102), and radiation is emitted from the radiation source 104. While the radiation is being emitted, the support article 110 is rotated about an axis 112, causing the object being examined (e.g., the prostate tumor and/or testicular tumor) to be viewed from multiple perspectives. Radiation that traverses the patient may be detected by the detector array 106 situated substantially opposite the radiation source 104 relative to the object. Signals 150 generated by the detector array 106 may be compiled and reconstructed to generate one or more three-dimensional images of the object, and the images may ultimately be used to develop a treatment plan for treating the tumor, for example.

In the example environment 100, a data acquisition component 126 is operably coupled to the imaging apparatus and is configured to receive the output signals 150 and/or other information from the imaging apparatus. Moreover, in the case of x-ray imaging (e.g., such as CT imaging), the data acquisition component 126 may also be configured to compile the output signals 150 received during a measuring interval (e.g., from the respective pixels) and generate projection space data 152. Such a compilation is at times referred to as a "view" or a "projection." In some embodiments, such as where the imaging apparatus is a CT scanner, a plurality of views may be generated from output signals 150 that are generated during an examination of the object/patient. Respective views may be indicative of a different relative orientation between the object and the radiation source 104. For example, a first view may comprise output signals generated while a patient was facing the radiation source 104 and a second view may comprise output signals 150 generated while the patient was facing away from the radiation source 104. Of course, there can be many more views (e.g., between these two views), and these two views are merely intended to be non-limiting examples.

In the example environment 100, the projection space data 152 is transmitted to an image reconstructor 128 configured to receive the projection space data 152. The image reconstructor 128 is also configured to use analytical, iterative, or other reconstruction techniques known to those skilled in the art (e.g., 2D filtered back projection, tomosynthesis reconstruction, etc.) to convert the projection space data 152 into one or more two-dimensional and/or three-dimensional images 154 of the object that are more perceptible to a human (e.g., relative to the projection data). Thus, the image reconstructor 128 converts that data from projection space to image space.

The example environment 100 also comprises a workstation 130 or terminal (e.g., a computer) configured to receive the one or more images 154. The two dimensional and/or three-dimensional image(s) 154 may be displayed on a monitor 131 of the terminal 130 to a user 132 (e.g., medical personnel). In this way, the user 132 can inspect the image(s) 154 to verify that a tumor is within the portion of the patient that is being examined, for example.

The terminal 130 may also be configured to receive user input from the user 132 which may provide instructions to a treatment plan determiner 134, a component of the imaging apparatus, and/or the support article 110, for example. In this way, a user 132 may provide input into the examination and/or the treatment of the patient, for example.

The example environment 100 also comprises a treatment apparatus configured to develop a treatment plan based at least in part upon the examination (e.g., imaging) of the object and to treat the object according to the treatment plan. As illustrated herein, in one embodiment, the treatment apparatus comprises a treatment plan determiner 134 and a radiation emission component 108, which includes a radiation nozzle from which treatment photons and/or particles (e.g., protons) are emitted.

The treatment plan determiner 134 is configured to receive information 156 (e.g., user input, image(s) 154, etc.) from the terminal 130 and/or projection space data 152 from the data acquisition component 126 and to use the received information to generate a treatment plan. It will be appreciated that by receiving projection space data 152 (e.g. instead of and/or in conjunction with the image(s) 154), the treatment plan determiner 134 may use data that may have fewer image artifacts, such as may be caused by the image reconstruction process, for example, and thus may more precisely identify a tumor, for example.

The treatment plan determiner 134 is configured to use the information 156 and/or the projection space data 152 to generate a treatment plan 158 for the object undergoing the operation. The treatment plan 158 may, among others things, specify the location, position, etc. of the tumor in the patient, the trajectory that radiation beams should travel (or rather, the orientation of a radiation nozzle emitting the beams of radiation relative to the object), the orientation of the support article and/or object/patent situated thereon relative to other components and/or the characteristics of the photons and/or particles to be used (e.g., the dose, the type of particles, etc.). In this way, it can be determined how to target tumor cells while mitigating impact to surrounding healthy tissue, for example. That is, it may specify a particular orientation of the support article 110 and/or the patient relative to the radiation nozzle, for example, to reduce and/or mitigate the amount/energy of the treatment radiation that traverses healthier tissue. For example, if the tumor is in the right breast, the treatment plan may specify one or more orientations that may desirably position the right breast relative to the radiation nozzle. The support article 110 may be tilted, raised, lowered and/or rotated, etc. for example, based upon the treatment plan such that the right breast is positioned as specified in the treatment plan (e.g., right breast is closer to radiation nozzle than left breast is to radiation nozzle). In this way, the right breast may, for example, be exposed to a larger amount and/or higher dosage of treatment radiation that the left breast and/or other tissues/organs of a patient (e.g. treatment radiation need not pass from the backside of the patient all the way through the patient to treat a region on the front of the patent). It will be appreciated that the treatment plan 158 may also comprise other information known to those skilled in the art and commonly included in a treatment plan for photon therapy and/or particle therapy techniques and/or systems.

As illustrated in the example environment 100, at least some portions of the treatment plan 158 may be transmitted to the terminal (e.g., so that the treatment plan 158 can be reviewed by a user 132), while the same or other portions may be transmitted to the imaging apparatus (e.g., so that a further examination can be performed if an adequate treatment plan cannot be developed), and/or a controller 136, for example. It will be appreciated that the treatment plan 158 may also and/or instead be delivered to other components not discussed herein but typically considered to be part of an imaging and/or treatment system for radiography therapy).

By way of example and not limitation, a treatment plan 158 may call for radiating a tumor with different doses of radiation photons and/or particles at different portions of the tumor. This may be accomplished, for example, by altering the power to the source of the radiation emission component 108 and/or rotating the support article 110 (e.g., causing the patient to be rotated such that different aspects of the tumor come in contact with the radiation beam (e.g., which follows a trajectory substantially out of the page) at different times).

The radiation emission component 108 is configured to generate and emit radiation beams that target a treatment region (e.g., as specified by the treatment plan 158). Generally, such a radiation emission component 108 generally comprises a plurality of components (not shown) that are used in the generation and subsequent emission of radiation treatment beams, which may be comprised of radiation photons and/or particles. For example, in one embodiment, the radiation emission component 108 comprises a radiation source, an accelerator, and a nozzle. It will be appreciated that while not illustrated herein, at least some of these components may be large and may be shared with multiple operation rooms similarly configured to the example operation room 102. Thus, as least some of the components comprised in the radiation emission component 108 may be comprised outside the operation room 102. For example, in one embodiment, merely the nozzle is comprised in the operation room 102 while other components of the radiation emission component 108 are comprised in other rooms proximate the operation room 102.

In one embodiment, a source component of the radiation emission component 108 is configured to generate and/or store photons and/or particles (e.g., protons, neutrons, ions, etc.) that are used to treat a tumor. For example, based upon information comprised within the treatment plan 158, the source may emit particles and/or photons with a particular characteristic. For example, the treatment plan 158 may specify a particular type of particle to be used and/or may specify a particular dose of photons, and the source component may generate and/or retrieve the specified particle and/or may generate the specified dose of photons, for example.

The radiation emission component 108 may also comprise an accelerator in one example. The accelerator is operably coupled to the source and may be configured to accelerate particles and/or photons emitted from the source 136 (e.g., such that the particles and/or photons emitted from the source are energized to a level that is specified in the treatment plan 158). In this way, in one example, the particles and/or photons may be specifically tailored to treat the treatment region within the patient while mitigating impact to other, healthier portions, of the patient which surround the tumor, for example. It will be appreciated to those skilled in the art that the accelerator may be comprised of a linear accelerator, a circular accelerator (e.g., a synchrotron or cyclotron), and/or another particle and/or photon accelerator known to those skilled in the art. Moreover, it will be appreciated that in another embodiment, the source may be able to generate the specified dose without the use of an accelerator, and thus, the radiation emission component 108 may not comprise an accelerator.

The radiation emission component 108 may further comprise a nozzle that is configured to emit radiation particles and/or radiation photons toward the object under examination, which is being treated by the treatment radiation. It will be appreciated that the orientation (e.g., position) of the nozzle with respect to the operation room 102 may remain substantially fixed while the object is being treated and/or the orientation/position of the nozzle may change. For example, in one embodiment, the nozzle may be configured for vertical motion (e.g., moving up and/or down the page (in the y-direction)) and/or horizontal motion (e.g., moving side to side (in the x-direction)). That is, the nozzle may be, but is not required to be, configured for movement (e.g., to facilitate "painting" a tumor).

In the illustrated example, the nozzle of the radiation emission component 108 is configured to emit one or more beams of treatment radiation (e.g., particles and/or photons) in a direction substantially out of a page (z-direction). That is, the treatment radiation generally traverses a plane that is substantially parallel to a plane of the floor 116 of the operation room. Thus, as illustrated herein, in one embodiment, the nozzle is configured to emit treatment radiation in a plane substantially parallel to a plane through which imaging radiation emitted from the radiation source 104 is emitted. Stated differently, the treatment apparatus and the imaging apparatus are configured to emit radiation in substantially parallel planes (e.g., and, in one embodiment, in the same plane (e.g., co-planar)), which are also substantially parallel to a plane of the floor 116 of the operation room 102, for example.

In one embodiment, the nozzle of the radiation emission component 108 is configured to steer or otherwise guide the beam of radiation (e.g., using actuators, scanning magnets, etc.) as specified in the treatment plan. In this way, mechanical limitations of the support article 112 (e.g., the ability of the support article 110 to position the object at a precise orientation relative to the nozzle within plus or minus 1 millimeter, for example) may be overcome by (slight) adjustments of the trajectory of the treatment radiation, for example. By way of example and not limitation, where the mechanical limitations of the support article 110 are on the order of a millimeter or so, but the nozzle of the radiation emission component 108 has sub-millimeter tolerances, such as 0.5 millimeter tolerances, for example, a particular area of interest can be more precisely targeted by "tuning" the nozzle instead of the support article 110.

It will be appreciated that while the nozzle may be used to fine-tune the trajectory of the treatment radiation (e.g., the particles and/or photons), the support article 110 may be configured to rotate and/or tilt the patient according to the treatment plan 158 to position the patient, and thus the tumor, for treatment. For example, as illustrated herein, the support article 110 may be configured to rotate about an axis 112 and/or tilt along an axis 118 to position the patient according to the treatment plan 158. In this way, the tumor may be treated from multiple angles, increasing the effectiveness of the radiation treatment, for example.

In the example environment 100, a controller 136 is also operably coupled to the treatment plan determiner 134 and the terminal 130. The controller 136 is configured to control the motion of the support article 110 based upon the treatment plan 158 and/or information 156 from the terminal 130 and/or to control the examination by the imaging apparatus. For example, the information 156 and/or the treatment plan 158 may specify an rpm for the support article 110 while the object is being examined by the imaging apparatus. Similarly, the information 156 and/or treatment plan 158 may specify an orientation (e.g., rotational angle, tilt, etc.) of the support article 110 (and thus an orientation of the object) relative to the imaging apparatus and/or the radiation emission component 108, for example. Thus, movement or other functions of the imaging apparatus and/or the radiation emission component 108 may be controlled by the controller 136. Moreover these interactions can be ongoing and/or adjusted (e.g., in real time). For example, because the treatment apparatus and the imaging/examination apparatus are co-located, the treatment (efficacy thereof) can be determined (e.g., by the imaging/examination apparatus) and adjustments made thereto (e.g., treatment dose, position of support article, etc.).

It will be appreciated that FIG. 1 (e.g., and the remaining figures) are merely intended to illustrate example components of a treatment apparatus comprising an imaging apparatus and a radiography treatment apparatus. That is, the examples described herein, including the placement of the components and/or the functions of respective components, are merely intended to generally describe some of the many components that typically are comprised in an imaging apparatus and/or a radiographic treatment apparatus and are not intended to be interpreted as limiting the scope of the disclosure, including the claims. For example, in another embodiment, the data acquisition component 126 may be part of a detector array 106 as opposed to a separate component of the example apparatus. Moreover, the components described herein may perform other and/or additional functions from those described herein. Thus, for example, the terminal 130 perform functions in addition to receiving/presenting image data 154 and receiving user input.

Figure 2:
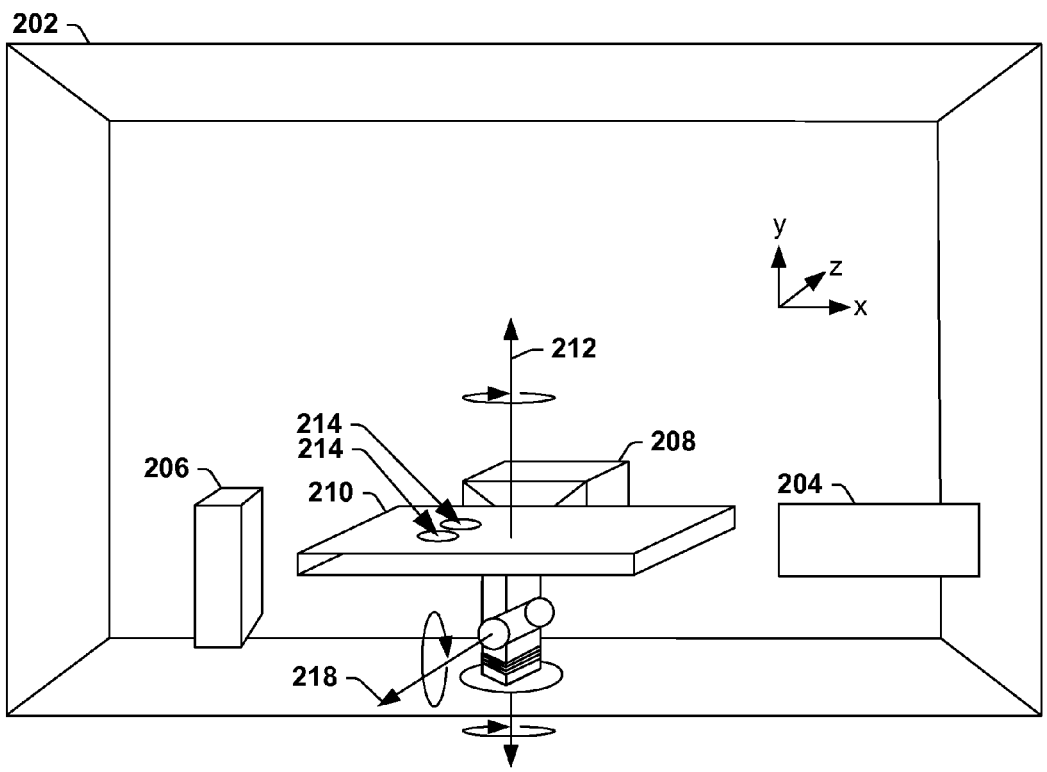
FIG. 2 illustrates an example environment for examining an object and treating the object using radiation.
Figure 3:
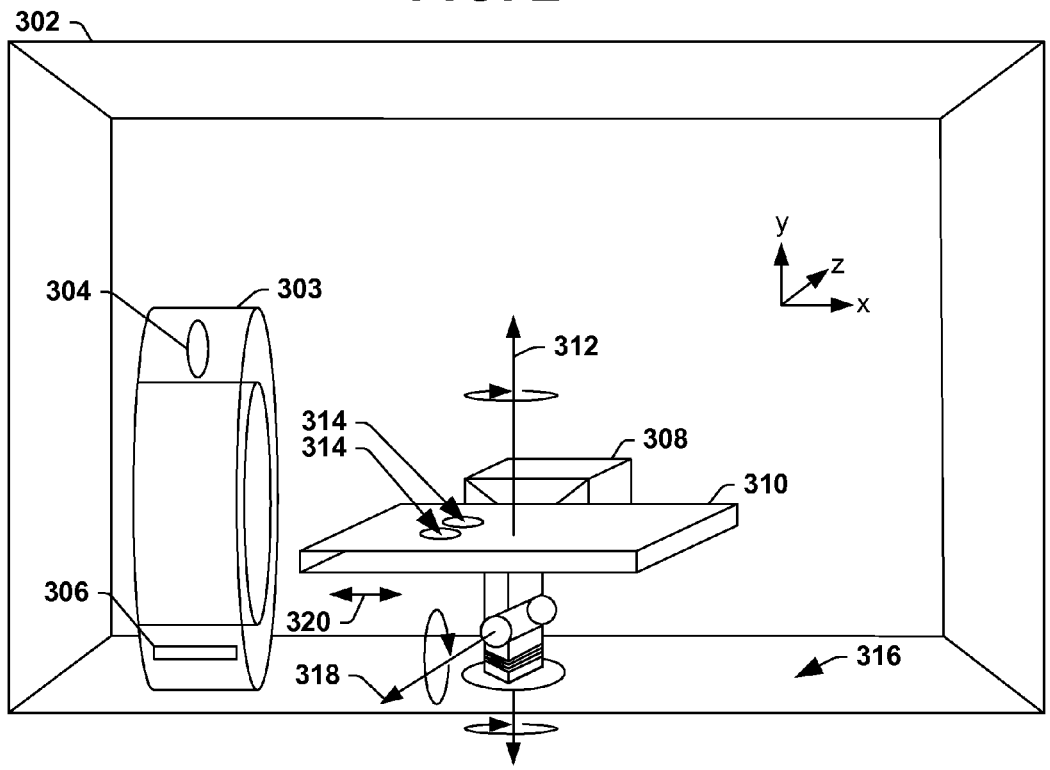
FIG. 3 illustrates an example environment for examining an object and treating the object using radiation.

FIGS. 2-3 respectively illustrate other embodiments of example operation rooms 202, 302 (e.g., 102 in FIG. 1), that may be better suited for some applications. For example, while a support article (e.g., 110 in FIG. 1) having a configuration similar to a chair may be beneficial in some applications (e.g., such as prostate cancer and/or testicular cancer treatment), in other applications, a support article that allows a patient to lay down may be beneficial (e.g., such as in breast cancer treatment, spinal cancer treatment, etc.).

FIG. 2 illustrates an example operation room 202 comprising an imaging apparatus (e.g., comprising a radiation source 204 (e.g., 104 in FIG. 1) and a detector array 206 (e.g., 106 in FIG. 1)) configured to examine an object under examination (e.g., a patient, or rather a portion of a patient that is undergoing treatment) and a radiation emission component 208 (e.g., 108 in FIG. 1) configured to treat the object using treatment radiation (e.g., radiation photons and/or radiation particles). It will be appreciated that for purposes of brevity, unless otherwise noted, the components illustrated in FIGS. 2-3 are substantially similar to their corresponding component illustrated in FIG. 1 (and a redundant discussion of the same is thus not included). Thus, the radiation emission component 208 may comprise components similar to those described with respect to FIG. 1 and/or may be configured to perform functions similar to those described in FIG. 1.

The operation room 202 further comprises a support article 210 (e.g., 110 in FIG. 1) configured to support the object while is it being examined and/or while it is being treated. It will be appreciated that the support article 210 is different that than the support article illustrated in FIG. 1 in that the support article 210 illustrated in FIG. 2 has a flat surface upon which a patient can lay. That is, the patient can be positioned on his/her/its back or in a prone position (e.g., with the patient lying on his/her/its stomach) during the examination. Moreover, in one embodiment, the support article 210 may comprise one or more receptors 214 (e.g. 114 in FIG. 1), for receiving a portion of the object under examination. Such receptors 214 may be holes or cavities in the support article 210, for example.

By way of example and not limitation, in one embodiment, the operation room 202 is configured to treat breast cancer and comprises a support article similar to that illustrated in FIG. 2, with a receptor(s) 214 for receiving breast tissue. Before the imaging and/or subsequent treatment begin, the patient lays on the support article in a prone position (e.g., and may be strapped in place to assist in immobilizing the patient) with his/her breast tissue positioned within the receptor(s) 214. An imaging apparatus (e.g., possibly comprising the radiation source 204 and the detector array 206) are configured to examine the breast tissue while the patient is laying on the support article 210 with the breast tissue still situated within the receptor(s) 214. A treatment plan may then be developed (e.g., which may take mere seconds to complete), and a treatment apparatus, which comprises the radiation emission component 208, may treat the breast tissue, or rather a treatment region within the breast tissue, with treatment radiation (e.g., photons and/or particles), while the patient continues to lay on the support article 210 with the breast tissue situated within the receptor(s) 214. In this way, the examination and the treatment of the patient may be performed while the patient remains in a substantially fixed orientation relative to the support article 210.

It will be appreciated that as described with respect to the support article 110 illustrated in FIG. 1, the support article 210 may be configured to rotate about an axis 212 and/or to tilt along a different axis 218. In this way, three-dimensional images (e.g., CT images) of the patient, or rather a portion of the patient that is to be treated, can be generated without rotating the imaging apparatus, for example. Further, rotating and/or tilting the support article 210 may assist the radiation emission component 208 in treating the tumor from a plurality of angles, for example. It will be appreciated that in another embodiment, the support article 210 may not rotate and thus portions of the imaging apparatus (e.g. the radiation source 204 and/or the detector array 206) and/or portions of the radiation emission component 208 may rotate about the support article 210, for example. Still, in other embodiments, the support article 210 and portions of the imaging apparatus and/or portions of the radiation emission component 208 may rotate.

Moreover, it will be appreciated that the support article herein described in FIGS. 1-3 may, in some embodiments, be at least partially constructed of materials that are transparent and/or partially transparent to radiation. In this way, the imaging radiation (e.g., if there is imaging radiation) and/or the treatment radiation may traverse the support article (e.g., 110, 210, 310 in FIGS. 1, 2, 3, respectively), substantially unimpeded, for example. For example, in one embodiment, portions of the support article 210 proximate the receptor(s) 214 may be comprised of a material(s) that is substantially transparent to radiation (e.g., such as a plastic), while other portions of the support article 210 may be comprised of a material(s) that is substantially opaque to radiation (e.g., such as lead). In this way, the imaging and/or treatment radiation can traverse the portion of the object/patient to be treated while reducing/minimizing radiation exposure to other portions of the object/patient that are not to be treated.

FIG. 3 illustrates yet another examination room 302 comprising an imaging apparatus 303 (e.g., possibly comprising a radiation source 304 (e.g., 104 in FIG. 1) and a detector array 306 (e.g., 106 in FIG. 1)) configured to examine an object under examination (e.g., a patient, or rather a portion of a patient that is undergoing treatment) and a radiation emission component 308 (e.g., 108 in FIG. 1) configured to treat the object using radiation (e.g., radiation photons and/or radiation particles).

As illustrated herein, the imaging apparatus 303 is configured similar to a conventional computed tomography (CT) scanner, wherein the radiation source 304 and the detector array 306 are coupled to a rotating gantry portion of the imaging apparatus 303. During an examination of the patient, the rotating gantry, and thus the radiation source 304 and the detector array 306 rotate about the patient. In this way, the patient may be examined from a plurality of perspectives, or angles, for example. It will be appreciated that while reference is made to imaging involving x-rays, other imaging devices, modalities, etc. are also contemplated. For example, in other embodiments, imaging may (also or alternatively) be performed using an MRI scanner and/or an ultrasound device.

In the illustrated embodiment, the radiation source 304 is configured to emit a fan, cone, or other shaped beam through a plane substantially perpendicular to a plane of the floor 316 (e.g., 116 in FIG. 1) of the operation room 302 and/or substantially perpendicular to a plane through which treatment radiation emitted from the radiation emission component 308 travels. However, in another embodiment, the imaging apparatus 303 may be positioned horizontally, such that the imaging beams travel through a plane substantially parallel to the floor 316 as described with respect to FIGS. 1 and 2.

The support article 310 is configured similarly to that described with respect to the support article 210 of FIG. 2. For example, the support article 310 may comprise one or more receptors 314 (e.g., 214 in FIG. 2) configured to receive a portion of the object under examination. Moreover, the support article may be configured to rotate, or pivot, about an axis 312 (e.g., 212 in FIG. 2) and/or tilt about a second axis 318 (e.g., 218 in FIG. 2), for example.

In one embodiment, the support article 310 may be further configured to move side-to-side 320 (e.g., right and left across the page). In this way, the object may be positioned within the imaging apparatus 303, for example. Moreover, in one embodiment, such a feature may help properly position the patient during treatment by the radiation emission component 308, for example. It will be appreciated that in another embodiment, the imaging apparatus 303 may be on glides, for example, and may be configured to move side-to-side and/or the radiation emission component 308 may be configured to move side-to-side. In such an embodiment the support article 310 may or may not be configured to move side-to-side, for example.

Figure 4:
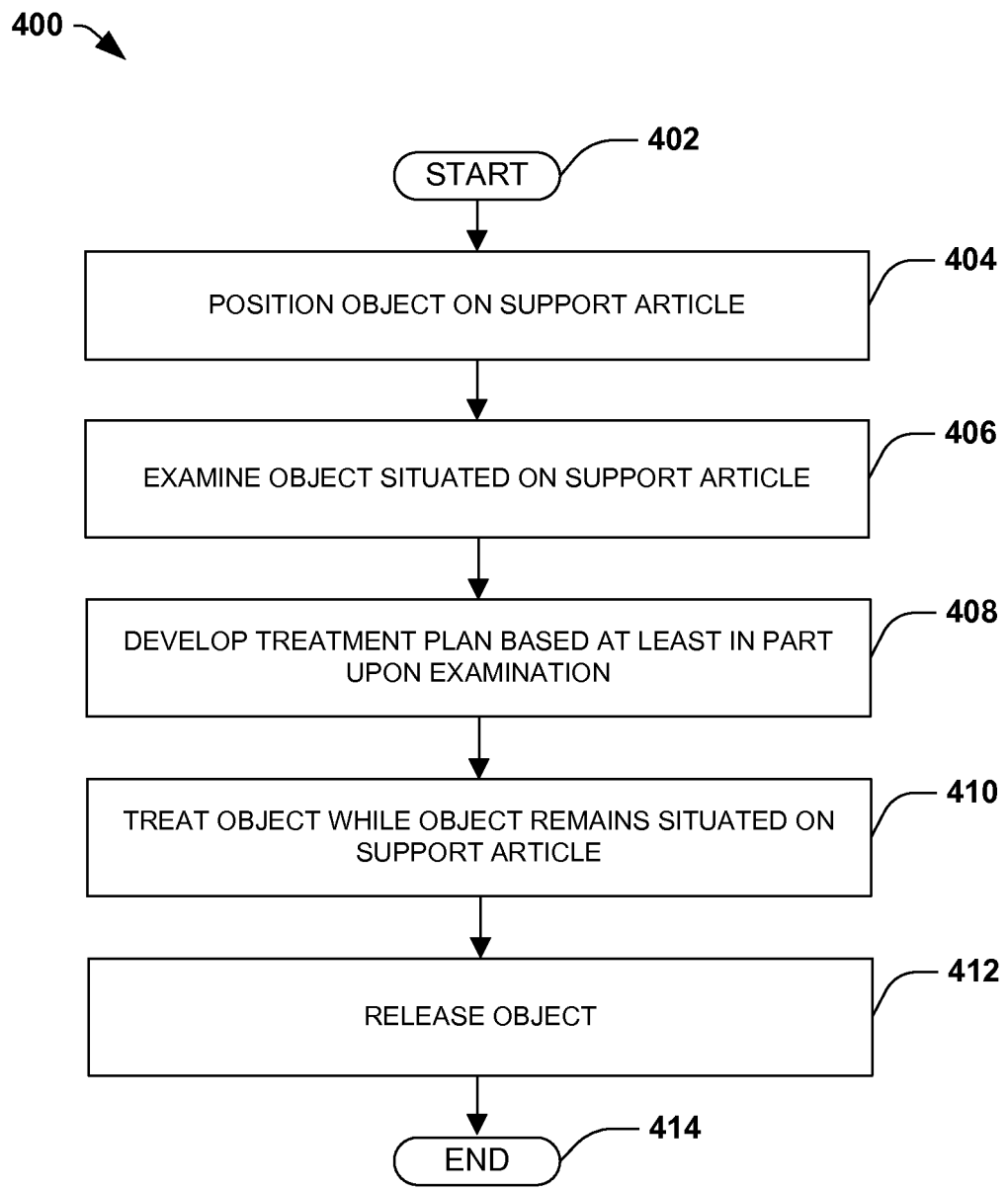
FIG. 4 is a flow diagram illustrating an example method of examining and treating an object using radiation while the object remains in a substantially fixed position.

FIG. 4 illustrates an example method 400. Such a method may be used to examine an object (e.g., a tumor and areas surrounding the tumor in a patient) and/or treat the object based upon a treatment plan developed from the examination. For example, such a method 400 may be used to acquire two-dimensional and/or three-dimension data and/or images indicative of, or representative of, the object and/or to treat a portion of the object being examined (e.g., a tumor) based upon a treatment plan yielded from the two- and/or three-dimensional data/images without changing the orientation and/or position of the object with respect to a support article upon which the object resides between the examination and the treatment.

The example method 400 begins at 402 and the object is positioned on a support article at 404. For example, in one embodiment, the object is positioned face down on a bed (e.g., a support article), configured to support the object during the examination and during the subsequent treatment. In another embodiment, the object may be seated in the support article and/or be positioned in an upright position on the support article, for example. Accordingly, unless specifically indicated, the scope of this application, including the claims, is not to be limited to a prone position.

As described above, in one embodiment, the support article may comprise one or more receptors through which and/or in which a portion of the object (e.g., a portion of a patient that comprises the tumor) is positioned. For example, in a breast cancer treatment facility, a portion of a patient's breast tissue may be positioned in the receptor(s) and/or in a prostate/testicular cancer treatment facility, a portion of a patient's prostate/testicular tissue may be positioned in the receptor. It will be appreciated that in other embodiments, the support article may not comprise such receptors (e.g., holes or crevices) designed to receive a portion of the object. For example, a patient may lay face-up on a support article with tissue to be examined and treated not comprised within, projecting through, etc. such receptors.

As part of the positioning at 404, the object may be secured to the support article or otherwise immobilized. For example, in one embodiment, the patient may be strapped or fastened to the support article to inhibit the patient's ability to accidently move during the examination and/or subsequent treatment, for example. In this way, the object may be held in a substantially constant position/orientation relative to the support article during both the examination and the treatment, for example.

At 406 in the example method 400, once the object is positioned or situated on the support article, the object is examined or imaged using an imaging system, such as one of the imaging systems described above. For example, in one embodiment, x-ray radiation is emitted from a radiation source aimed at the object under examination. Radiation that traverses the object is detected by a detector array positioned on a substantially opposite side of the object relative to the radiation source, and signals indicative of the detected radiation are generated. These signals may then be compiled and/or reconstructed using one or more techniques known to those skilled in the art (e.g., 2D filtered back projection, tomosynthesis reconstruction, etc.) to generate one or more two-dimensional and/or three-dimensional images of an object under examination. In this way, planar or volumetric data of an object under examination may be acquired, for example. However, other techniques (e.g., such as MRI techniques and/or ultrasound techniques) known to those skilled in the art are also contemplated.

It will be appreciated that in order to generate volumetric data (e.g., and thus three-dimensional images), the object is generally imaged from a plurality of angles or perspectives. For example, in a computed tomography application, objects are generally imaged from at least 180 degrees to generate the volumetric data. Thus, the object and/or the imaging apparatus (e.g., the radiation source and/or the detector array) is generally rotated during the examination if volumetric data is required and/or preferred for the application. In one embodiment, as described above with respect to FIGS. 1-3, the support article (e.g., and thus the object, or patient being supported by the support article) are configured to rotate, or pivot, about an axis during the examination of the object while the imaging apparatus is maintained in a substantially fixed position (e.g., the imaging apparatus does not move). It will be appreciated that the speed of rotation may a function of the imaging apparatus (e.g., the support article may rotate at a speed that produces higher (e.g., optimal) resolution images). In another embodiment, the support article may be maintained in a substantially fixed position while a portion(s) of the imaging apparatus rotates about the object, and in still another embodiment, both the support article and a portion(s) of the imaging apparatus rotate about the object. Thus, the instant application, including the scope of the claims, is to the extent practical not intended to be limited to a rotating support article and/or a rotating imaging apparatus.

At 408 in the example method 400, a treatment plan for treating the object is developed based at least in part upon the examination (e.g., and/or images resulting from the examination). The treatment plan comprises an identification of a treatment region (e.g., which may be smaller, the same size as, or larger than the object being treated (e.g., a tumor in the patient)) that will be targeted by a beam(s) of treatment radiation (e.g., radiation photons and/or particles). The treatment plan may also comprise, among other things, information regarding the trajectory of the beam(s), the dose of the treatment radiation, the duration of the treatment, etc. It will be appreciated that such information can be, at least partially determined, based upon the size and/or orientation of the tumor as determined from the images, or from the data acquired, during the examination of the object that occurred at 406.

Once a treatment plan is developed (e.g., which may take a matter of seconds to a few minutes to develop) and while the patient remains situated on the support article, the object, or rather the treatment region of the object, may be treated using treatment radiation at 410 in the example method 400. It will be appreciated that numerous treatment radiations are known to those skilled in the art and are contemplated for use herein. For example, in one embodiment, a tumor within the object is treated using radiographic particles (e.g., protons). In another embodiment, a tumor is treated using radiographic photons. Thus, the instant application, including the scope of the claims, is not intended to be limited, to the extent practical, to a particle type of radiation therapy treatment. Rather, the type of treatment may depend upon, among other things, the size of the object being treated (e.g., the size of the tumor) and/or the location of the tumor relative to other objects within a patient (e.g., how close the tumor is to vital organs that are susceptible to radiation exposure).

During the treatment one or more beams of radiation are emitted towards the treatment region of the object (e.g., as specified in the treatment plan). These beams are generally targeted towards a specific portion of the treatment region, and in one embodiment, travel through a plane that is substantially parallel to a plane through which radiation used for examining the object traveled (e.g., as illustrated in FIG. 1). In another embodiment, the treatment radiation traverses a plane substantially perpendicular to a plane through which radiation used for examining the object traveled (e.g., as illustrated in FIG. 3).

To assist in targeting a specific portion of the treatment region (e.g., as specified by the treatment plan), in one embodiment, the support article is configured to rotate during the treatment. For example, a first beam of treatment radiation targeting a first portion of a tumor may be emitted, a support article (e.g., and thus a patient on the support article) may be rotated, and a second beam of treatment radiation targeting a second portion of the tumor may be emitted. In this way, the tumor may be treated from different sides, angles, etc. and/or painted with treatment radiation, for example. In another embodiment, the support article is not configured to rotate, and portions of a radiation emission component from which treatment radiation is emitted may be rotated or otherwise moved, for example.

It will be appreciated that because the object is positioned at 404 prior to the examination and remains in the same position during both the examination and the subsequent treatment, the position or orientation of the tumor is substantially fixed, or held constant. In this way, the treatment region may be smaller than the conventional treatment region, which may mitigate impact to surrounding healthy tissue. Stated differently, because the orientation of the tumor remains substantially constant between the imaging and the treatment, the treatment region does not have to be enlarged (e.g., at least not to as great of an extent) to compensate for changes in the orientation of the tumor between the examination and the subsequent treatment, for example. It will be appreciated that because examination/imaging of the object and treatment of the object are performed substantially concurrently (e.g., by a treatment apparatus and an imaging/examination apparatus that are co-located), the treatment (efficacy thereof) can be determined (e.g., by the imaging/examination apparatus) and adjustments made thereto (e.g., treatment dose, position of support article, etc.) substantially in real time. For example, treatment can occur, then examination, then (adjusted) treatment, then examination, then (adjusted) treatment, etc. For example, an initial treatment plan may call for exposing a tumor to two doses of treatment radiation before rotating the support article (and patient) to expose an opposite side of the tumor to a dose of treatment radiation, but an examination of the tumor after the first dose of treatment radiation may reveal that the first dose was quite effective. Accordingly, the support article (and patient) may be rotated after merely the first dose.

At 412 in the example method 400, the object is released. That is, after the examination and treatment are complete, the patient is allowed to get up from the support article, for example.

At 414 the example method 400 ends.

Figure 5:
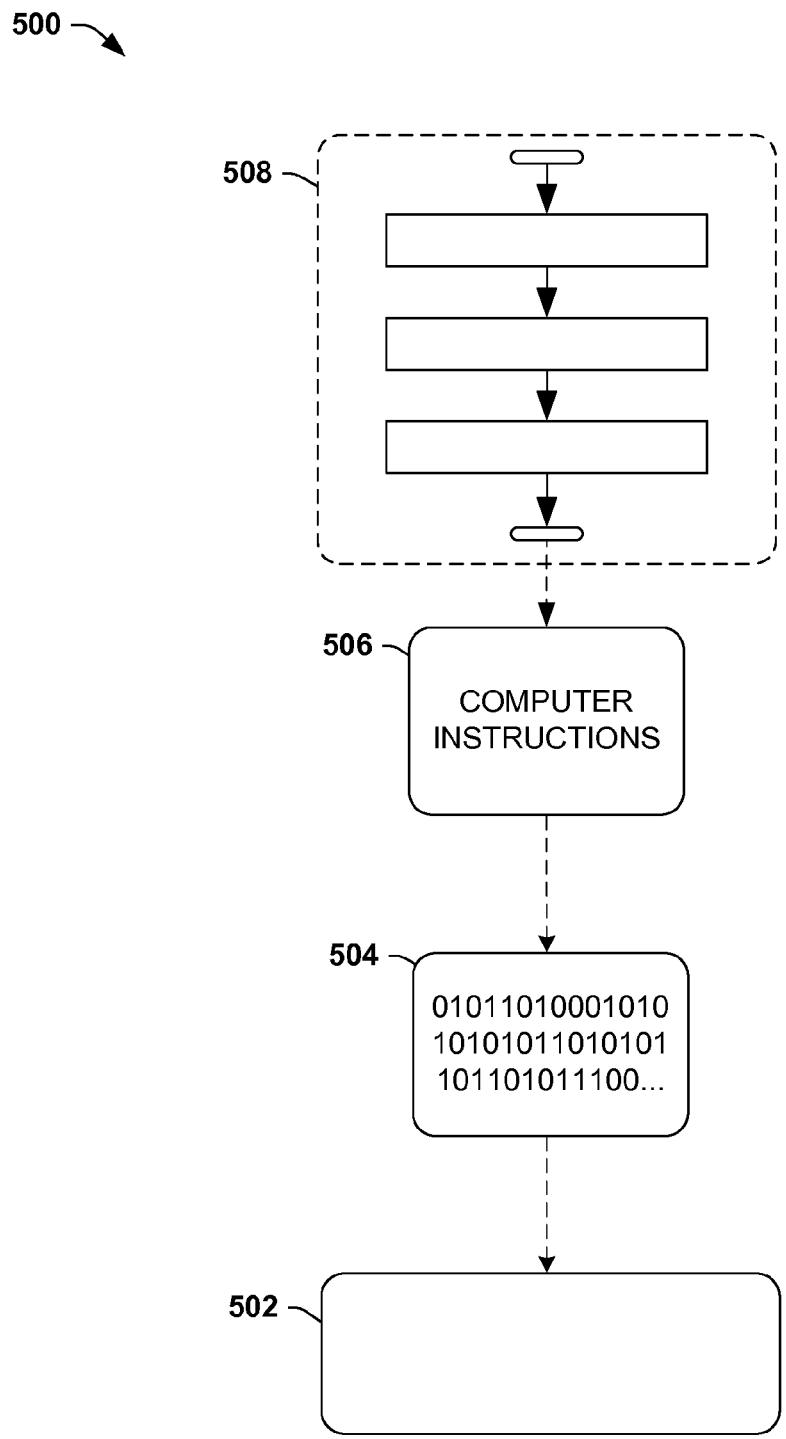
FIG. 5 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 5, wherein the implementation 500 comprises a computer-readable medium 502 (e.g., a flash drive, CD-R, DVD-R, or a platter of a hard disk drive), on which is encoded computer-readable data 504. This computer-readable data 504 in turn comprises a set of computer instructions 506 configured to operate according to one or more of the principles set forth herein. In one such embodiment 500, the processor-executable instructions 506 may be configured to perform a method 508, such as at least some of the example method 400 of FIG. 4, for example. In another such embodiment, the processor-executable instructions 506 may be configured to implement a system, such as at least some of the exemplary system 100 of FIG. 1, for example. Many such computer-readable media may be devised by those of ordinary skill in the art that are configured to operate in accordance with one or more of the techniques presented herein.

Moreover, the words "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form. Also, at least one of A and B and/or the like generally means A or B or both A and B.

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. An apparatus, comprising:
   an imaging apparatus configured to perform an examination on an object;
   a treatment apparatus configured to develop a treatment plan based at least in part upon the examination and to perform a treatment on the object according to the treatment plan; and a support article configured to support the object in a substantially same orientation relative to the support article during both the examination and the treatment, the support article comprising one or more receptors for receiving at least a portion of the object and configured to pivot about an axis of rotation during at least one of the examination or the treatment.

2. The apparatus of claim 1, the support article substantially affixed to a floor of an operation room during both the examination and the treatment.

3. The apparatus of claim 1, the imaging apparatus configured to examine the object using x-ray radiation.

4. The apparatus of claim 3, the imaging apparatus configured to emit the x-ray radiation into a first plane and the treatment apparatus configured to emit photon radiation in a second plane substantially parallel to the first plane.

5. The apparatus of claim 4, the first plane and the second plane being substantially co-planar.

6. The apparatus of claim 1, the object comprising at least part of a patient, and the patient positioned in a prone position on the support article.

7. The apparatus of claim 1, the object comprising breast tissue and the one or more receptors configured to receive at least a portion of the breast tissue.

8. The apparatus of claim 1, the object comprising at least one of prostate tissue or testicular tissue and the one or more receptors configured to receive at least a portion of the at least one of prostate tissue or testicular tissue.

9. The apparatus of claim 1, the imaging apparatus configured to generate three-dimensional image data of the object under examination.

10. The apparatus of claim 1, the imaging apparatus remaining substantially fixed during the examination.

11. A method comprising:
examining an object situated on a support article to develop a treatment plan;
treating the object based upon the treatment plan while the object remains situated on the support article; and
rotating the object and the support article about an axis of rotation during at least one of the examining or the treating, the support article substantially affixed to a floor of an operation room during both the examining and the treating.

12. The method of claim 11, the examining comprising examining the object to generate three-dimensional image data of the object.

13. The method of claim 11, comprising maintaining an imaging apparatus configured to perform the examining in a substantially fixed position during the examining.

14. The method of claim 11, the examining comprising emitting x-ray radiation in a first plane.

15. The method of claim 14, the treating comprising emitting photon radiation in a second plane, the second plane substantially parallel to the first plane.

16. The method of claim 11, the examining and the treating performed while the object is in a prone position on the support article.

17. The method of claim 11, the object remaining in a substantially fixed orientation relative to the support article during both the examining and the treating.

18. The method of claim 11, the examining comprising rotating at least one of an x-ray source or a detector array relative to the object to generate three-dimensional image data of the object.

19. The method of claim 11, comprising:
identifying a treatment area based upon the examining, wherein the treating comprises using radiation photons to treat the treatment area.

20. An apparatus for treating at least one of breast cancer, prostate cancer or testicular cancer, comprising:
a support article comprising a receptor for receiving at least one of breast tissue, prostate tissue or testicular tissue of a patient;
an imaging apparatus configured to perform an examination on the at least one of breast tissue, prostate tissue or testicular tissue while the patient is supported by the support article; and
a treatment apparatus configured to perform a treatment on the at least one of breast tissue, prostate tissue or testicular tissue while the patient is supported by the support article,
the support article configured to pivot about an axis during at least one of the examination or the treatment causing a position of the at least one of breast tissue, prostate tissue or testicular tissue to change relative to at least one of the imaging apparatus or the treatment apparatus,
the examination and the treatment performed while the patient remains in a substantially fixed orientation relative to the support article.

* * * * *